(12) United States Patent
Booth et al.

(10) Patent No.: US 6,440,080 B1
(45) Date of Patent: Aug. 27, 2002

(54) AUTOMATIC OSCILLOMETRIC APPARATUS AND METHOD FOR MEASURING BLOOD PRESSURE

(75) Inventors: John W. Booth; Bruce A. Friedman, both of Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 09/962,380

(22) Filed: Sep. 25, 2001

(51) Int. Cl.[7] ................................................. A61B 5/00
(52) U.S. Cl. .................... 600/494; 600/495; 600/496
(58) Field of Search ............................ 600/490, 493–6

(56) References Cited

U.S. PATENT DOCUMENTS

| | | |
|---|---|---|
| 4,349,034 A | 9/1982 | Ramsey, III |
| 4,360,029 A | 11/1982 | Ramsey, III |
| 4,425,920 A | 1/1984 | Bourland et al. |
| 4,543,962 A | 10/1985 | Medero et al. |
| 4,638,810 A | 1/1987 | Ramsey, III et al. |
| 4,793,360 A * | 12/1988 | Miyawaki et al. ........... 600/494 |
| 4,869,261 A | 9/1989 | Penaz |
| 4,873,987 A | 10/1989 | Djordjevich et al. |
| 4,889,133 A | 12/1989 | Nelson et al. |
| 4,949,710 A | 8/1990 | Dorsett et al. |
| 5,054,494 A * | 10/1991 | Lazzaro et al. ............. 600/494 |
| 5,178,154 A | 1/1993 | Ackmann et al. |
| 5,590,662 A | 1/1997 | Hersh et al. |
| 5,649,543 A | 7/1997 | Hosaka et al. |
| 5,785,659 A | 7/1998 | Caro et al. |
| 5,865,755 A | 2/1999 | Golub |
| 6,186,953 B1 | 2/2001 | Narimatsu |

* cited by examiner

Primary Examiner—Robert L. Nasser
(74) Attorney, Agent, or Firm—George E. Haas; Quarles & Brady LLP

(57) ABSTRACT

Blood pressure of an human being is read by a process that places a cuff around a portion of the human being's body. The cuff is inflated to a predefined pressure which occludes the flood of blood and then the cuff is deflated in a controlled manner. At a plurality of deflation pressure levels, pressure pulses that occur in the cuff are integrated to produce a plurality of integral values. A diastolic pressure of the human being is derived in response to the deflation pressure level at which occurred the integral value that is greatest in magnitude.

20 Claims, 2 Drawing Sheets

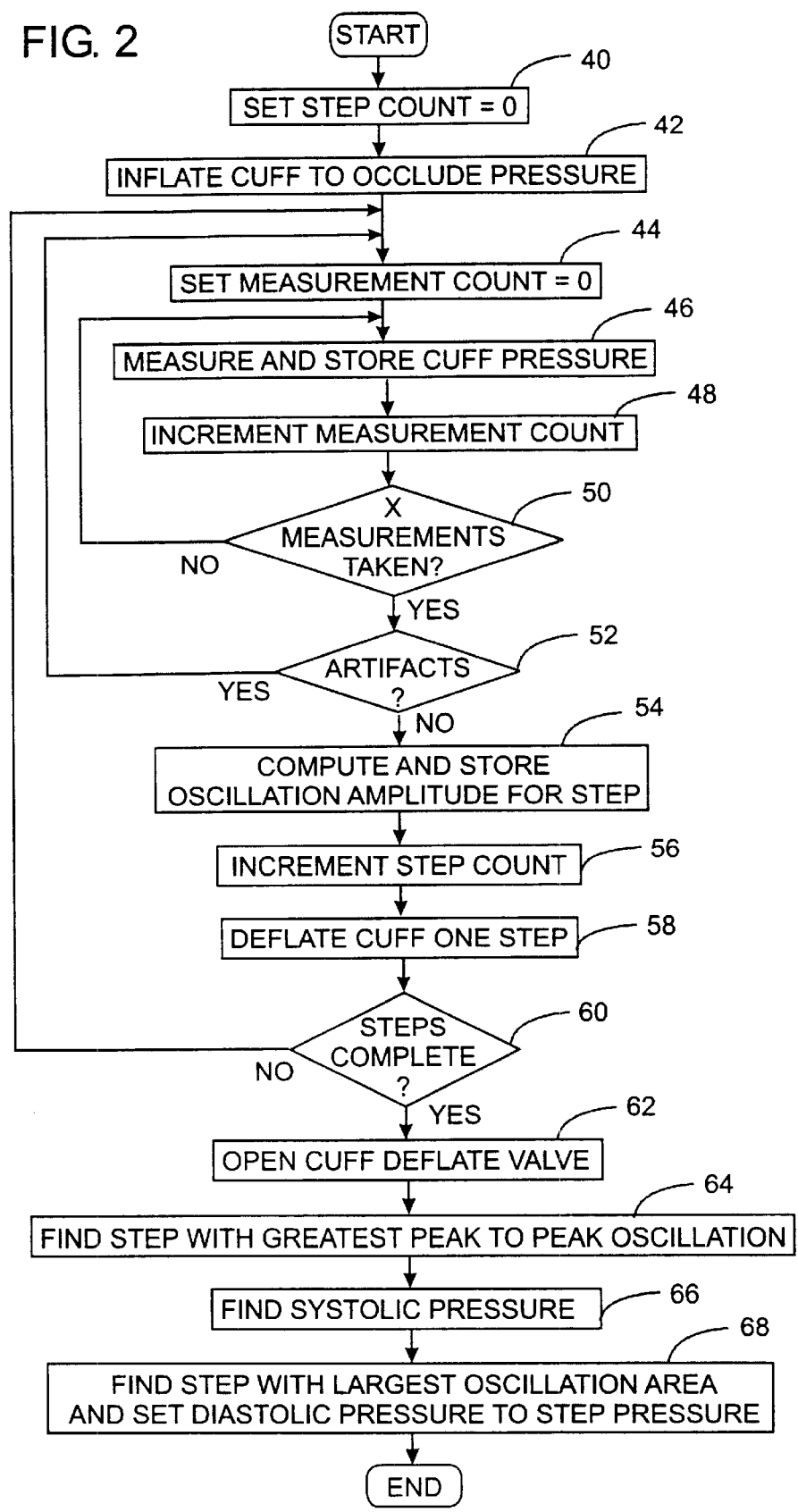

AUTOMATIC OSCILLOMETRIC APPARATUS AND METHOD FOR MEASURING BLOOD PRESSURE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention generally relates to oscillometric blood pressure determining techniques, and more particularly to determining the diastolic pressure using that technique.

Knowing the pressures exerted by blood on the blood vessel walls of patients is of great value to those engaged in medical practice. In the case of humans, the pressure in the vascular system is measured for many reasons, including diagnosis, ascertainment of the progress of therapy, the physiological state when under anesthesia, etc. As an example, the determination of arterial blood pressure is an essential element in the diagnosis of a patient suspected of cardiac disease. Normal human arterial blood pressure ranges between 80–120 millimeters of mercury, whereas elevations of arterial blood pressure above that range are found in cases of congestive heart failure, renal artery disease, coarctation of the aorta, etc. Additionally, untreated hypertension is known to be associated with an increased risk of stroke, coronary artery disease, and aneurysms.

During the cycle of the heartbeat, which normally occurs approximately once per second, the arterial blood pressure oscillates. When the heart muscle contracts, known as systole, blood is pushed into the arteries. This increases the arterial pressure. When the heart muscle relaxes, known as diastole, the arterial blood pressure falls. The maximum of the arterial pressure oscillation during the heartbeat is known as systolic pressure; the minimum is known as diastolic pressure. The arterial pressure versus time waveform can also be used to calculate what is known as mean arterial pressure. The mean arterial pressure (MAP) is calculated by integrating the arterial pressure waveform for one cycle and then dividing that quantity by the cycle period. The indirect techniques of oscillometry and auscultation are used in practice to estimate the systolic, mean, and diastolic pressures non-invasively. However, it is known that under certain rare conditions the diastolic estimate which oscillometry produces is inaccurate, yet the systolic and MAP estimates are good. It is the purpose of this invention to improve the diastolic estimate using easily obtained, but previously ignored oscillometric information.

The auscultatory method is commonly used by medical personnel to indirectly measure arterial blood pressure. In this technique, constrictive pressure is gradually applied about the limb of the patient until the flow of blood through the limb vessel has been arrested, as determined by listening to a stethoscope applied over the vessel at a point distal the point of constriction. Then upon gradual release of the constriction pressure, the beginning of the flow through the vessel can be heard and the constriction pressure is noted on a gauge reading in millimeters of mercury. This pressure is referred to as systolic pressure and is taken as an estimate of the true intra-arterial systolic pressure. The pressure then is gradually released further until the sounds of the flow again cease and the pressure is again noted, which pressure is referred to as diastolic pressure and is taken as an estimate of the true intra-arterial diastolic pressure. The difference between the diastolic pressure and systolic pressure is termed pulse pressure. Previously the constriction pressure has been derived from an inflatable cuff connected to a mercury column manometer or to an aneroid type gauge having a dial scale calibrated in millimeters of mercury. It is also known that the auscultatory estimate of diastolic pressure can at times be inaccurate; auscultation can be very technique dependent and varies, for example, due to the hearing ability of the clinician taking the reading. Furthermore, auscultation can, in some cases, be quite confusing when determining diastolic estimates because the Korotkoff sounds may never disappear as the cuff pressure is lowered.

A previous automatic indirect blood pressure reading apparatus employed the oscillometric method in which an arm cuff is inflated to a pressure at which blood flow is occluded. The cuff then is deflated at predetermined pressure increments in a step-wise manner. At each step, the pressure in the cuff is measured repeatedly using a suitably short sampling period in order to detect pressure fluctuations. The instantaneous pressure in the cuff is due to the inflation pressure and the force exerted by the pressure pulsations in the patient's blood vessels during each heartbeat. The beating heart causes the pressure in the cuff to oscillate at each step of deflation. The apparatus continues in this fashion until a complete envelope of oscillation amplitude versus cuff pressure is obtained. The cuff pressure at which the maximum amplitude oscillations are obtained is indicative of the mean arterial pressure. The systolic and diastolic pressure estimates are also determined from predefined functions of the envelope data. The oscillometrically determined systolic, MAP, and diastolic are considered estimates of the true intra-arterial pressure values. However, it is also known that arterial compliance plays a major role in the estimating functions; arterial compliance can change in complicated and unpredictable ways as physiological circumstances change.

BRIEF SUMMARY OF THE INVENTION

The oscillometric blood pressure is determined indirectly from a cuff that is placed around a portion of the body, such as an upper arm, of the human being whose blood pressure is desired. The cuff is inflated to a predetermined pressure, preferably great enough to occlude the flow of blood in the limb of the patient. Then the cuff is deflated in a controlled manner to produce a deflation pressure in the cuff that decreases with time. In the preferred embodiment, the cuff is deflated in regular pressure increments thereby producing a plurality of discrete deflation pressure levels.

During each of a plurality of heartbeats, the pressure oscillations that occur at the discrete deflation pressure levels are measured and stored in the apparatus. The complete data set of the amplitude of the oscillations versus the discrete pressure levels is known as the oscillometric envelope. The oscillometric estimate of the mean arterial pressure is determined from this envelope data. For example, the estimate of the mean arterial pressure (MAP) is the deflation pressure level that occurs when the oscillation measurements have the greatest amplitude. Similarly, the systolic pressure can be estimated from the envelope data by finding the discrete pressure level which occurred when the oscillation amplitude is a predetermined fraction of the maximum oscillation size at cuff pressures above MAP. Note that interpolating between discrete deflation pressure levels may produce a more accurate estimate of systolic pressure.

Diastolic pressure can be estimated from the envelope data by finding the discrete pressure level which occurred when the oscillation amplitude is a predetermined fraction of the maximum oscillation size at cuff pressures below MAP. Interpolating between discrete deflation pressure levels may produce a more accurate estimate of diastolic pressure. This method can lead to errors in the determination of diastolic pressure under some circumstances.

In the preferred embodiment, the diastolic pressure is determined by measuring the area of the oscillation complexes. The diastolic pressure is determined by finding the deflation pressure below MAP that produces the largest oscillation area.

If for a given measurement, the measured amplitude under the oscillation pulse is greatest at MAP, then the diastolic pressure will be determined from the deflation pressure where the oscillation amplitude is a predetermined fraction of the maximum amplitude.

In an alternative embodiment, the diastolic pressure is determined by finding a first deflation pressure at which the maximum oscillation area occurs and a second deflation pressure at which the predetermined amplitude ratio occurs. The diastolic pressure is calculated as the average of the first and second deflation pressures.

DESCRIPTION OF THE OF THE DRAWINGS

FIG. 2 is flowchart of the operation of the apparatus;

DETAILED DESCRIPTION OF THE INVENTION

Figure 1:
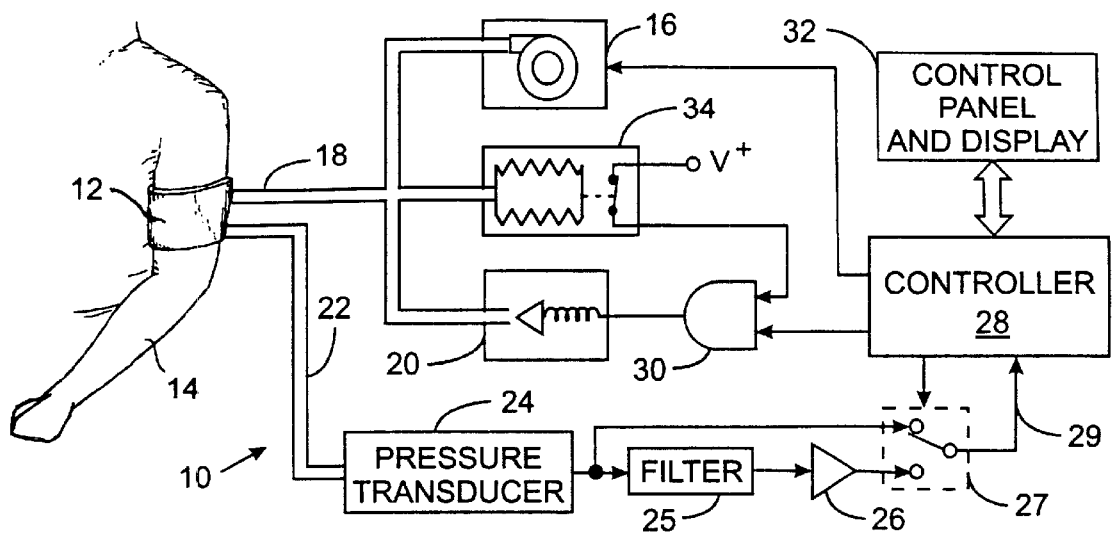
FIG. 1 is a block diagram of an indirect noninvasive apparatus for measuring blood pressure.

With reference to FIG. 1, an automatic blood pressure measuring apparatus 10 employs an inflatable cuff 12 shown wrapped around an arm 14 of a human medical patient. The inflatable cuff 12 is connected to a pump 16 by a flexible first tube 18. The first tube also connects to an electrically operated deflation valve 20 and to a protective over pressure switch 34 which responds to excessive pressure being applied to the cuff 12. A flexible second tube 22 couples the cuff 12 to a pressure transducer 24 which produces an electrical signal at output that indicates the pressure within the cuff.

The output of the pressure transducer 24 is connected directly to one input of a multiplexer 27. The pressure transducer output also is coupled to a band pass filter 25 which in turn is connected to an amplifier 26 which has an output connected to another input of the multiplexer 27. The filter 25 and amplifier 26 are designed to reject the d.c. component of pressure signal produced by the transducer 24 and yet amplify the blood pressure oscillations, as will be described. Specifically, the filter 25 passes those signals having frequency components in an approximate range of one to ten Hertz and strongly rejects other frequency components. The amplifier 26 magnifies low level signals from the filter 25. The output signal from the amplifier 26 corresponds to the oscillations, or the a.c. component, of the pressure in the cuff 12. These components have been used in previous blood pressure sensors and are well known to those skilled in the art. Alternatively, the unfiltered cuff pressure signal could be used if it has enough analog to digital conversion resolution.

The multiplexer 27 selects one of the two pressure signals and couples the selected signal to an analog input 29 of a controller 28. The controller 28 is a computerized device which includes a conventional microprocessor, a memory for storing a program that controls operation of the apparatus 10 and data used in the execution of that program, and input and output circuits to interface the controller to other components of the apparatus. For example, the output of the multiplexer 27 is connected to an input of an internal analog to digital converter of the controller 28. A control panel and display 32 provides a user interface to the blood pressure measuring apparatus. The controller 28 has an output connected to control the pump 16.

Another output of the controller 28 is coupled to a first input of an AND gate 30. The AND gate 30 has a second input connected to the over pressure switch 34 and an output that connects to control the deflation valve 20. In the event of an excessive pressure in the cuff 12, the over pressure switch 34 opens which results in the output of the AND gate opening the deflation valve 20 to relieve that excessive pressure in the cuff 12. Additional devices can be provided to alert the attending personnel to abnormal pressure or functional conditions.

In operation, the cuff 12 is wrapped around the arm 14 of a patient whose blood pressure is to be measured. The attendant then activates a switch on the control panel 32 which commences the measurement operation. Specifically, the controller 28 responds to the electrical signal produced when that switch is operated by commencing execution of a control program which performs a measurement cycle.

With reference to FIG. 2, the control program commences at step 40 with the controller 28 initializing a step count to a value of zero. At step 42, the controller produces output signals which close the deflation valve 20 and activatea the pump 16 to inflate the cuff 12. As the cuff is being inflated, the controller 28 monitors the electrical signal from the pressure transducer 24 which indicates the pressure within the cuff 12. The cuff is inflated to a predefined pressure which is known to occlude the flow of blood within the blood vessels of the arm 14. For example, if previous pressure measurements have been taken from this patient, the occlude pressure may be a predefined amount (e.g. 60 mm of mercury) greater than the previous systolic pressure. Once this occlude pressure has been obtained, the controller 28 terminates operation of the pump 16 while maintaining the deflation valve 20 in a closed state.

Figure 3:
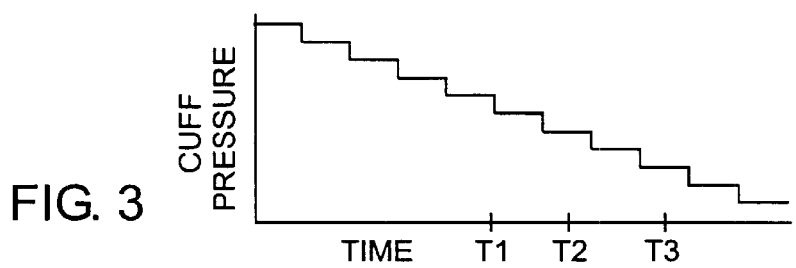
FIG. 3 is a graph of pressure in a cuff of the apparatus.

The controller 28 then begins a controlled deflation of the cuff 12 while periodically measuring the pressure therein. In the preferred embodiment of the present invention, the controller gradually deflates the cuff in a series of steps as shown in FIG. 3 and the nominal pressure at each step is referred to herein as the "deflation pressure" or the "deflation step pressure". For example, each step may be a decrease in pressure of eight millimeters of mercury. As noted previously the instantaneous pressure at each step is not always constant, but oscillates slightly due to the force exerted on the cuff 12 by the blood pulsing through the patient's blood vessels. A plurality of pressure measurements are taken at each step to measure those pressure oscillations. As will be described, the systolic and diastolic pressures are derived from an analysis of the pressure fluctuations at the different pressure steps. Alternatively, the pressure within the cuff can be deflated in a continuous, preferably linear, manner while continuously measuring the pressure fluctuations within the cuff 12. As a further alternative, the cuff pressure measurements used to estimate the patient's blood pressure can be acquired while the cuff is being inflated.

The pressure measuring begins at step 44 where the controller 28 sets a measurement count to zero. The execution of the software program then enters a loop at which a plurality of measurements of the pressure within the cuff 12 are taken. At step 46, the signal from the pressure transducer 24 is read by the controller 28 and stored in memory. The signal produced by the pressure transducer 24 can be read directly to sense the deflation step pressure and then the pressure signal processes by the band pass filter 25 and amplifier 26 can be read to obtain a measurement of the amplitude of the blood pressure oscillation waveform. Specifically the filter and amplifier remove the baseband or d.c. offset of the pressure measurement that is due to the deflation step pressure leaving only the a.c. component representing the oscillation waveform. Then, the measurement count is incremented at step 48 before the program advances to step 50 where a determination is made whether the requisite number of measurements, designated by the variable X, has been taken at this pressure step. If not, the program execution loops back to step 46 to acquire another measurement.

The requisite number of measurements determines the length of time that the apparatus remains at each pressure step of the deflation process. The requisite number X is large enough to ensure that the pressure will be measured over at least one cardiac cycle. When that number of measurements has been taken, the program execution advances to step 52 at which the measurements for the current step are analyzed to determine whether they contain artifacts which will interfere with accurate blood pressure determination. As is well known, artifacts can be produced by arm movement during the sensing or by an attendant bumping against the cuff. Various processes exist for detecting these artifacts, such as described in U.S. Pat. No. 4,349,034, the description of which is incorporated by reference. If a significant artifact is found, the program execution returns to step 44 to acquire another set of measurements at the present deflation step. This loop continues until satisfactory measurements are taken or until a determination is made by the controller 28 that accurate measurement is not possible.

Figure 4:
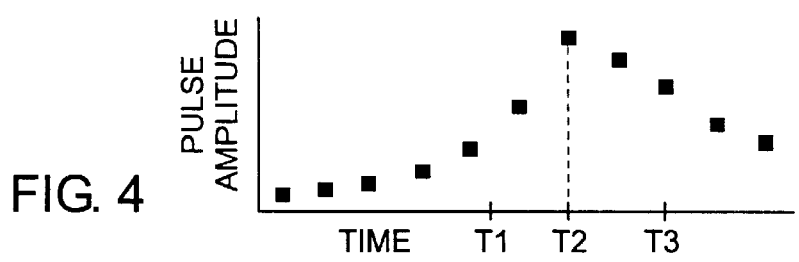
FIG. 4 is a graph of the amplitude of the oscillation pulses of the cuff pressure.
Figure 5:
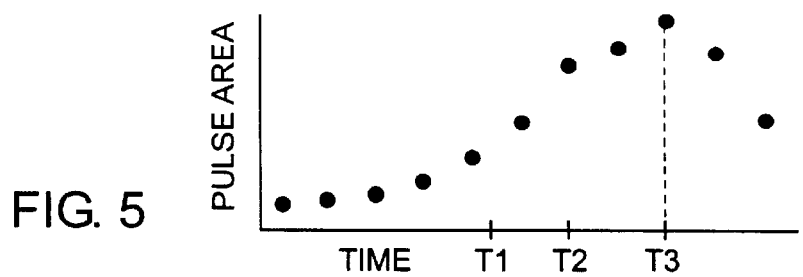
FIG. 5 is a graph of the area of the oscillation pulses.

Once a valid set of pressure measurements has been acquired for a given pressure step, the program execution advances to step 54 where the maximum oscillation amplitude for that step is computed. As the pressure within the cuff is released, the force exerted on the cuff by the arterial blood flow produce greater oscillations of the cuff pressure. In other words, when the pressure in the cuff is relatively high, only the pressure peaks of each pulse of blood in the patient's arm exceed the deflation cuff pressure so as to vary the total cuff pressure. As the cuff 12 is deflated further, a greater portion of each blood pressure pulse exceeds the deflation cuff pressure, thereby producing pressure oscillations with larger amplitudes as depicted in FIG. 4. Therefore, at step 54, the controller 28 calculates the difference between the greatest pressure measured during the step and the deflation pressure of that step. That difference is stored in memory as the pulse or oscillation amplitude for the associated deflation pressure step.

The operation of the measurement apparatus then proceeds to step 56 where the deflation step count is incremented. Next at step 58, the controller opens the deflation valve 20 to release a given amount of pressure within the cuff 12. The controller 28 directly monitors the signal from the pressure transducer 24 until the pressure has decreased by the desired amount, for example eight millimeters of mercury. Then a determination is made at step 60 whether the requisite number of pressure steps has been completed for the measurement cycle. The measurement cycle may be defined in terms of a given number of steps, or dynamically by observing the oscillation amplitudes measured for each step, the measurement cycle can terminate when those amplitudes are not longer changing.

Upon completion of the measurement cycle, the controller 28 opens the deflation valve 20 at step 62 to release any remaining pressure within the cuff 12. Then at step 64, the controller examines the oscillation amplitudes stored in memory for each of the deflation steps. Specifically, the stored value representing the greatest oscillation amplitude is located, as occurred for example at time T2 in FIG. 4, and the deflation step pressure at that time is identified. That step pressure corresponds to the mean arterial pressure (MAP). At step 66 the systolic pressure is derived by first calculating a reference peak oscillation amplitude that is given fraction (e.g. 0.5) of the greatest oscillation amplitude. The deflation step pressure at the time T1 when that reference peak oscillation amplitude first occurred is found. The deflation pressure at that step then corresponds to the systolic pressure. The peak oscillation amplitude of any deflation step may not correspond exactly to the calculated reference peak oscillation amplitude. In which case the reference peak oscillation amplitude falls between the peak oscillation amplitudes of two adjacent deflation steps. When that occurs, the systolic pressure is derived by interpolating the deflation pressures for those steps.

The present inventor has found that the diastolic pressure occurs at the highest deflation pressure at which the oscillations have the greatest area. In other words, the diastolic pressure of the patient can be derived by integrating pressure measurements for each deflation step and finding deflation cuff pressure of the deflation step at which the greatest integral occurred. This is accomplished at step 68 by summing the pressure measurements during each deflation step and identifying the first deflation step to occur that is associated with the largest sum. The deflation pressure for that step corresponds to the diastolic pressure.

Therefore, the present apparatus determines the systolic pressure based on a fraction of the mean pressure during the measurement cycle, and determines the diastolic pressure based on an integral of the pressure oscillations which occur during each step; and specifically, based on the deflation pressure which occurs at a step that has the greatest integral.

As a variation of the method by which the diastolic pressure value is determined, the integration procedure described above is used to produce a first estimate of the diastolic pressure. Then a second estimate of the diastolic pressure is derived by first calculating a reference value that is given fraction of the greatest oscillation amplitude. The deflation step that occurred after the occurrence of the greatest oscillation amplitude are inspected to find the step having a peak oscillation amplitude that is closest arithmetically to the reference value. The deflation pressure at that step then is defined as the second estimate of the diastolic pressure. That second estimate also can be derived by interpolating the deflation pressures for adjacent deflation steps between which the reference value is located. The a diastolic pressure value then is determined by averaging the first and second estimates of the diastolic pressure, although other arithmetic functions can be employed to derive the diastolic pressure value from those estimates.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

What is claimed is:

1. A method for indirectly measuring blood pressure comprising:

placing a cuff around a portion of a human being;

varying pressure within the cuff to produce a plurality of cuff pressure levels;

while at a given cuff pressure level, measuring and storing the given cuff pressure level and a plurality of pressure oscillation amplitude values to produce a pressure oscillation waveform, thereby producing a plurality of measurements;

integrating a plurality of pressure oscillations of the pressure oscillation waveform to produce a plurality of integral values; and deriving a first estimate of diastolic pressure for the human being in response to the cuff pressure level which occurred coincident with the pressure oscillation which produced the integral value that is greatest in magnitude.

2. The method as recited in claim 1 wherein the integrating comprises individually summing pressure oscillation amplitude values which correspond to each of the plurality of pressure oscillations.

3. The method as recited in claim 1 wherein varying pressure within the cuff comprises inflating the cuff.

4. The method as recited in claim 1 wherein varying pressure within the cuff comprises inflating the cuff to a predetermined pressure, and thereafter deflating the cuff to produce the plurality of pressure levels which decrease with time.

5. The method as recited in claim 1 further comprising:

determining a peak value for each pressure oscillation;

identifying a peak value of greatest magnitude;

deriving a second estimate of diastolic pressure which corresponds to the cuff pressure level which occurred coincident with the pressure oscillation that has the peak value of greatest magnitude; and calculating a diastolic, pressure value as a function of the first estimate of diastolic pressure and the second estimate of diastolic pressure.

6. The method as recited in claim 5 wherein calculating a diastolic pressure value averages the first estimate of diastolic pressure and the second estimate of diastolic pressure.

7. The method as recited in claim 1 further comprising determining an estimated mean arterial pressure for the human being from the plurality of measurements.

8. The method as recited in claim 1 further comprising determining an estimated systolic pressure for the human being from the plurality of measurements.

9. A method for indirectly measuring blood pressure comprising the steps of:

(a) placing a cuff around a portion of a human being's body;

(b) inflating the cuff to a predetermined pressure;

(c) periodically measuring pressure in the cuff thereby producing an oscillation pressure waveform;

(d) deflating the cuff by a predetermined increment of pressure, which results in a deflation pressure in the cuff;

(e) repeating the steps (c) and (d) for a plurality of times thereby producing a plurality of oscillation pressure waveforms;

(f) utilizing an oscillometric technique to estimate a systolic pressure and a mean arterial pressure for the human being from a plurality of oscillation amplitudes derived from the oscillation pressure waveforms;

(g) integrating the plurality of measurements taken during each different deflation pressure to derive an integral value for each different deflation pressure; and (h) deriving a first estimate of diastolic pressure of the human being from the deflation pressure associated with the greatest integral value.

10. The method as recited in claim 9 further comprising:

identifying a separate peak value for each of the plurality of oscillation pressure waveforms;

identifying a peak value of greatest magnitude;

deriving a second estimate of diastolic pressure which corresponds to the deflation pressure which occurred coincident with the oscillation pressure waveform that has the peak value of greatest magnitude; and calculating a diastolic pressure value as a function of the first estimate of diastolic pressure and the second estimate of diastolic pressure.

11. The method as recited in claim 10 wherein calculating a diastolic pressure value averages the first estimate of diastolic pressure and the second estimate of diastolic pressure.

12. The method as recited in claim 9 wherein the step of integrating the plurality of measurements comprising separately summing a plurality of measurements.

13. The method as recited in claim 9 wherein the step of inflating the cuff to a predetermined pressure comprising activating an electrically operated pump.

14. The method as recited in claim 9 wherein the step of deflating the cuff comprises opening an electrically controlled valve for a period of time.

15. The method as recited in claim 9 wherein deflating the cuff comprises opening an electrically controlled valve, measuring pressure in the cuff, and closing the electrically controlled valve when the pressure in the cuff has decreased by the predetermined increment.

16. An apparatus for producing information indicative of blood pressure of an human being through indirect measurement comprising:

an inflatable cuff;

a pump connected to the cuff, for inflating the cuff to a pressure above systolic pressure of the human being;

a deflating valve connected to the cuff to release fluid from within the cuff thereby varying pressure within the cuff;

a transducer that measures pressure oscillations in the cuff caused by heartbeats of the human being; and a controller responsive to the transducer for initially energizing the pump to inflate the cuff and subsequently energizing the deflating valve incrementally to deflate the cuff at predetermined pressure increments, wherein the controller integrates the pressure oscillations occasioned by successive heartbeats to produce a plurality of integral values and identifies as a diastolic pressure, the pressure which occurs in the cuff when the pressure oscillations have an integral value of greatest magnitude.

17. The apparatus as recited in claim 16 wherein the controller integrates the pressure oscillations by summing a plurality of measurements of pressure in the cuff acquired from the transducer during each heart beat.

18. The apparatus as recited in claim 16 wherein the controller further includes:

a mechanism that identifies a peak value for the pressure oscillations during each heartbeat, a calculator that derives a value which is a predefined fraction of the greatest peak value;

means for identifying, as a systolic peak value, a peak value that is closest arithmetically to the greatest peak value; and an element that determines a systolic pressure of the human being in response to the deflation pressure which occurred during the same heart beat as the systolic peak value.

19. The apparatus as recited in claim 16 wherein the controller activates the deflating valve periodically to deflate the cuff at predetermined pressure increments.

20. The apparatus as recited in claim 16 wherein further including a mechanism that responds to an excessive pressure in the cuff by activating the deflating valve.

* * * * *